United States Patent [19]

Nedbaluk

[11] Patent Number: 5,078,696
[45] Date of Patent: Jan. 7, 1992

[54] NEEDLE CAPPING DEVICE

[76] Inventor: Mike S. Nedbaluk, 62 Dowing Estates 53049, R.R. 220, Ardrossan, Alberta, Canada, T0B 0E0

[21] Appl. No.: 544,523

[22] Filed: Jun. 28, 1990

[30] Foreign Application Priority Data

Jun. 30, 1989 [CA] Canada .................................. 604606

[51] Int. Cl.<sup>5</sup> ............................................. A61M 5/32
[52] U.S. Cl. .................................... 604/192; 604/263
[58] Field of Search ...................... 604/192, 187, 263

[56] References Cited

U.S. PATENT DOCUMENTS

| | | | |
|---|---|---|---|
| 3,993,063 | 11/1976 | Larrabee | 604/187 |
| 4,122,836 | 10/1978 | Burnett | 604/187 |
| 4,559,042 | 12/1985 | Votel . | |
| 4,573,975 | 3/1986 | Frist et al. . | |
| 4,629,453 | 12/1986 | Cooper | 604/192 |
| 4,717,386 | 1/1988 | Simmons . | |
| 4,735,617 | 4/1988 | Nelson et al. | 604/192 |
| 4,737,149 | 4/1988 | Gillilan | 604/263 X |
| 4,742,910 | 5/1988 | Staebler | 604/263 X |

FOREIGN PATENT DOCUMENTS 2209470 5/1989 United Kingdom ................ 604/263
85/03006 7/1985 World Int. Prop. O. .......... 604/192

*Primary Examiner*—John D. Yasko
*Attorney, Agent, or Firm*—Murray E. Thrift; Stanley G. Ade; Adrian D. Battison

[57] ABSTRACT

Designed for use primarily with needles carrying radioactive material in which the syringe is inserted into a radiation shield, the device includes a freestanding support having a planar shield on the upper end of a stem extending upwardly from a base. A central aperture through the shield and into the stem includes an upstanding portion having a chamfered outer end. The lower end of the radiation shield surrounding the syringe includes an inwardly tapered or chamfered bore so that self centering takes place as the syringe and needle is inserted into the stem. The device also allows one handed insertion of the syringe and needle into the sheath which is in the bore of the stem leaving the other hand free to attend or support the patient. If held by the stem in the other hand, the shield prevents the needle from engaging the hand or fingers of the operator as the needle is reinserted into the sheath.

14 Claims, 1 Drawing Sheet

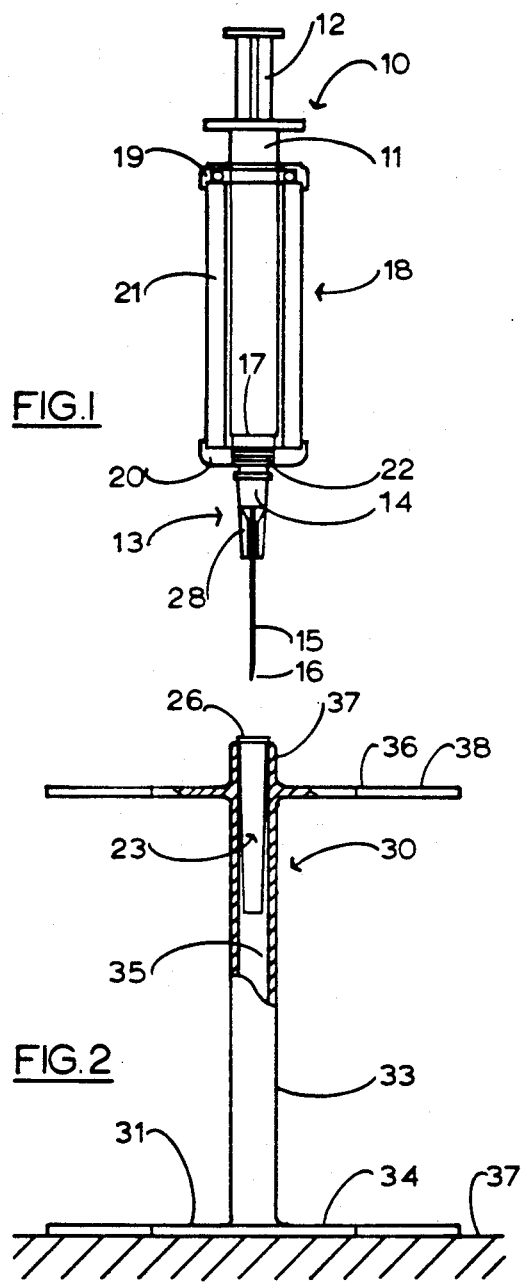
FIG.1
FIG.2
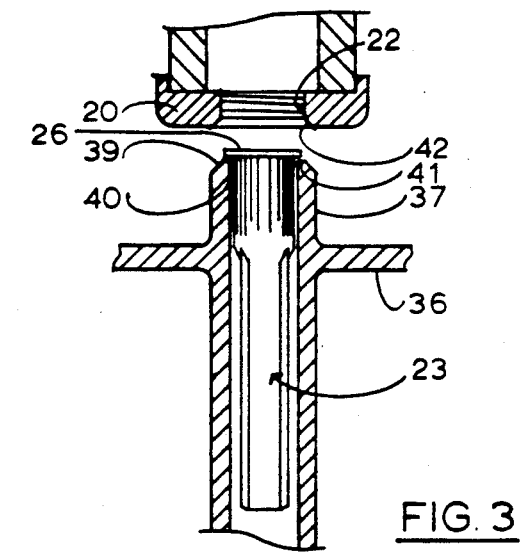
FIG.3
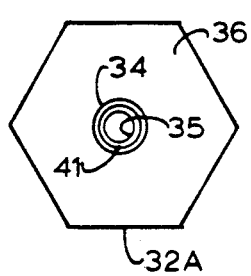
FIG.4
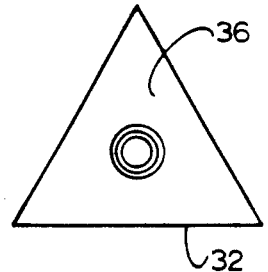
FIG.5
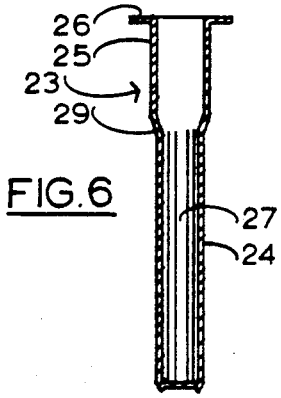
FIG.6
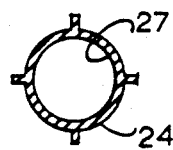
FIG.7

NEEDLE CAPPING DEVICE

FIELD OF THE INVENTION

This invention relates to new and useful improvements in needle capping devices, specifically devices which assist the operator to insert a hypodermic needle into the sheath thereof without any danger of the needle engaging the fingers or hand of the operator.

BACKGROUND

Needle assemblies used for injections, extraction of blood and the like, from patients or animals include a syringe part with a detachable hypodermic needle on one end thereof and normally enclosed within a plastic sheath which frictionally engages the inner end of the needle assembly after the needle has been inserted into the sheath. Operators such as nurses, doctors, medical technicians, veterinary doctors, and radiological technicians often use disposable needle and syringe assemblies for various purposes during the treatment of patients. After use, the needle is with the sheath associated therewith prior to disposal.

This recapping process conventionally consists of holding the plastic sheath in one hand and the needle assembly in the other whereupon the operator endeavours to engage the extremely sharp extremity of the needle into the relatively small bore of the sheath. This often results in the operator missing the sheath altogether and whereby the sharp end of the needle penetrates the skin of the operator either on the fingers or hand thereof. With present day dangers of infection being transferred from the patient to the operator, it is desirable that some means be provided whereby such inadvertent puncturing is alleviated or prevented from occurring all together, and although the device is designed specifically for use with needle and syringe assemblies surrounded by a radiation shield, nevertheless it may be used with other types of needle and syringe assemblies.

According to one aspect of the present invention there is provided a support and retainer for syringe and needle combinations comprising in combination:

an elongate stem having upper and lower ends, at least a portion of the stem adjacent the upper end being hollow;

a base secured to the lower end of the stem for supporting the stem in an upright position on a substantially flat, horizontal surface; and a shield extending around the stem adjacent the upper end thereof.

In accordance with another aspect of the invention, there is provided a support for use with a syringe and needle combination in which said syringe and needle combination includes a syringe, a hypodermic needle detachably secured to one end of said syringe, a selectively detachable sheath for said needle and a radiation shield component, said radiation shield component including a rear cap and a front cap with a substantially cylindrical radiation shielding element therebetween, said front cap being centrally apertured, said central aperture being screw threaded to screw threadably receive the front end of the associated syringe, said support including:

an elongate stem with upper and lower ends, at least a portion of the stem adjacent the upper end being hollow;

a base secured to the lower end of the stem for supporting the stem in an upright position on a substantially flat, horizontal surface; and a shield extending around the stem adjacent the upper end thereof.

The support can be engaged upon a flat surface such as a table whereon it is self supporting. The sheath is supported in the hollow upper end of the stem. The needle of the syringe and needle combination is then easily engaged within the sheath, utilizing only one hand thereby permitting the operator to use the other hand to support or attend to a patient. The capping apparatus can be used to support a needle and syringe combination which may be used upon one patient intermittently such as, for example, a dentist applying an anaesthetic at several locations within the mouth of the patient.

The configuration of the outer perimeter of the base and shield may be such that, if the device is rested horizontally upon a flat surface, it cannot roll or move from the location in which it is placed.

BRIEF DESCRIPTION OF THE DRAWINGS

With the foregoing in view, and other advantages as will become apparent to those skilled in the art to which this invention relates as this specification proceeds, the invention is herein described by reference to the accompanying drawings forming a part hereof, which includes a description of the best mode known to the applicant and of the preferred typical embodiment of the principles of the present invention, in which:

FIG. 1 is a side elevation of a needle and syringe assembly within a radiation shield.

FIG. 2 is a fragmentary vertical cross-sectional view of the invention showing the needle sheath inserted therein.

FIG. 3 is a fragmentary enlarged exploded view of the upper end of the stem showing the method of centering the radiation shield thereon.

FIG. 4 is a top plan view of FIG. 2 but with the sheath removed.

FIG. 5 is a top plan view of FIG. 2 but showing an alternative configuration of the shield and base.

FIG. 6 is an enlarged cross-sectional view of the sheath per se.

FIG. 7 is a view along the line 7—7 of FIG. 6.

In the drawings like characters of reference indicate corresponding parts in the different figures.

DETAILED DESCRIPTION

Proceeding therefore to describe the invention in detail, reference should first be made to FIG. 1 which shows a needle and syringe assembly collectively designated 10 including a conventional syringe 11 having a cylindrical barrel and an operating plunger 12. A needle assembly collectively designated 13 includes the plastic inner end portion 14 and a hypodermic needle 15 extending therefrom which of course is hollow and includes the extremely sharp penetrating end 16. This needle assembly is normally screw threadably engaged within the discharge end 17 of the barrel 11.

Reference character 18 illustrates generally, a conventional radiation shield assembly including a rear cap 19, a front cap 20 and a substantially cylindrical leaded glass radiation shield barrel 21 extending therebetween. The end caps 19 and 20 are apertured centrally to receive the syringe 11 with the discharge end 17 being screw threadably engageable within the screw threaded aperture specifically designated 22 in the front end cap 20 so that the needle assembly 13 extends beyond the shield. Such radiation shields are normally used by nuclear medical technologists and this use requires that the needle assembly which contains the radioactive material, must be capped with the sheath collectively designated 23, during insertion into the radiation shield in order to prevent any possibility of contamination occurring to the needle assembly. This sheath 23, which is conventional, is normally made of plastic and consists of the main elongated hollow body portion 24, and enlarged upper end 25 and an extending upper flange 26. The interior of the portion 24 is provided with longitudinally extending grooves 27 which receive longitudinally extending ribs 28 normally formed on the outer surface of the tapered body portion 14 of the hypodermic needle portion 13 so that when it is necessary to re-engage the needle with the sheath, the needle is engaged within the sheath until the ribs 28 reach the area 29 at the junction between the grooves 27 and the portion 25 whereupon a slight rotation of one or the other enables the ribs to engage the grooves and to slide down into full engagement and frictional retention of the sheath upon the needle assembly and it is this action which normally holds danger of the needle piercing the operator.

The invention collectively designated 30 is preferably made of stainless steel o another material that can be sterilized or autoclaved between use. It consists of a planar base portion 31 which is provided with an outer perimeter 32 of at least three straight edges as shown in FIG. 5 thus forming a triangular configuration when viewed in plan. However, the preferred configuration is shown in FIG. 4 which shows six straight sides 32A thus forming a regular hexagon. This prevents the apparatus from rolling if it is positioned on its side on a flat surface. Other non-circular shapes can be used for the periphery of the base if desired.

A stem 33 is secured to and extends upwardly from the upper surface 34 of the base 31 and centrally thereof and this stem is preferably hollow for at least the major portion of the length thereof thus defining a bore 35 extending from the upper end downwardly towards the base.

A planar shield 36 is secured around the stem spaced downwardly from the upper end 37 thereof and the external configuration and size of this shield is preferably the same as the base 31 with the straight sides 32 or 32A in alignment between the shield 36 and the base 31. The shield 36 is spaced and parallel to the base so that the operator may grasp the stem 33 in one hand with the base 31 being on one side of the fist formed to grasp the stem and the shield 36 on the other side with the fingers and hand being fully shielded by the shield 36.

Alternatively, the stand or device 30 may be placed upon a planar surface 37 such as a table or the like so that the device is self supporting upon the base 31 and extends upwardly from the surface 37.

The upper end portion 37 of the stem which extends above the upper surface 38 of the shield 36 is provided with an upwardly and inwardly inclining upper end 39 which terminates outwardly of the inner wall 40 of the bore thus defining an inner annular upper side portion 41 perpendicular to the longitudinal axis of the bore 35 as shown in FIG. 3, the purpose of which will hereinafter become apparent.

Reference to FIG. 3 will also show the inner end cap 20 of the radiation shield which is screw threaded centrally as at 22. The outer ends of the screw threaded portion 22 extend upwardly and inwardly as indicated by reference character 42 which matches substantially the chamfer or upwardly or inwardly extending surface 39 at the top end of the stem 33.

In use, and dealing first with the radiation shield covered syringe and needle assembly 10, the needle has been engaged with the radiation shield 18 whereupon the sheath 23 is either removed manually from the needle assembly 13 and engaged within the upper end of the stem as shown in FIG. 2, or, alternatively, the entire needle assembly with sheath is engaged downwardly within the stem 30 whereupon the sides of the bore within the stem 33 holds the sheath frictionally and allow the needle assembly and radiation shield assembly to be withdrawn ready for use.

Once the hypodermic needle assembly has been used on the patient, and the stand is engaged upon a planar surface 37, it is easy to re-engage the needle assembly 13 downwardly within the sheath 23 rotating same slightly so that the ribs 28 engage the grooves 27, and either withdraw the entire sheath needle assembly for disposal or let the stand 30 support the needle assembly which extends upwardly from the upper end 37 of the stem.

It will be noted that this may be a one-handed operation thus leaving the other hand of the operator free to support or attend to the patient upon whom the needle assembly has been used. It will also be note that the device will support the needle assembly if intermittent use upon the same patient is required.

If used with the radiation shield assembly 18, and if it is now ready for disposal, the entire syringe can be unscrewed from the radiation shield assembly and withdrawn therefrom together with the sheath which is now engaged upon the needle, whereupon the syringe and needle assembly can be disposed of in a conventional manner.

It will be noted, upon reference to FIG. 3, that when the sheath 23 is engaged within the upper end of the stem 33, the flange 26 engages the inner annular upper side portion 41 of the upper end 37 of the stem but that the flange does not intrude upon the chamfer 39 so that centering of the needle assembly by engaging the chamfer 42 of the shield with the chamfer 39 of the upper end, is relatively easy and which thus assists in the engagement of the needle body 14 with the sheath portion 24 without damage occurring to the needle. This is particularly useful when intermittent use of the one needle assembly is desired.

It will also be appreciated that the device can be used upon syringe and needle combinations without the radiation shield and that the sheath 23 can either be engaged within the stem 33 prior to disengagement from the needle 13 or, alternatively, the sheath can be removed and placed within the stand prior to use of the needle.

It will also be noted that the stand may be grasped by one hand of the operator around the stem and between the base 31 and the shield 36 so that the needle can be engaged within the sheath 23 supported within the bore, without any danger of the needle engaging the skin of the fingers or hand of the operator.

Since various modifications can be made in my invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

I claim:

1. A support and retainer for syringe and needle combinations comprising in combination:

an elongate rigid stem having upper and lower ends, at least a portion of the stem adjacent the upper end being hollow and an outer side of the stem adjacent the upper end of said stem tapering upwardly to an annular upper end face;

a base comprising a rigid flange with a non-circular periphery secured to the lower end of the stem for supporting the stem in an upright position on a substantially flat, horizontal surface; and a shield comprising a plate with a non-circular periphery extending around the stem adjacent the upper end of the stem, with the upper end of the stem extending above the shield.

2. The combination according to claim 1 in which the base has a triangular periphery.

3. The combination according to claim 1 in which the base has an hexagonal periphery.

4. The combination according to claim 2 in which the shield is a plate which has a triangular periphery.

5. The combination according to claim 3 in which the sheild is a plate with an hexagonal periphery.

6. A support for use with a syringe and needle combination in which said syringe and needle combination includes a syringe having a front end and a rear end, screw threads on the front end of the syringe, a hypodermic needle detachably secured to the front end of said syringe, a selectively detachable sheath for said needle and a radiation shield component, said radiation shield component including a rear cap and a front cap with a substantially cylindrical radiation shielding element therebetween, said front cap having a central aperture therein, screw threads in said central aperture to mate with the front end of the associated syringe, said support including:

an elongate stem with upper and lower ends, at least a portion of the stem adjacent the upper end being hollow;

a base secured to the lower end of the stem for supporting the stem in an upright position on a substantially flat, horizontal surface; and a shield extending around the stem adjacent the upper end thereof.

7. The support according to claim 6 in which said base comprises a flange with a non-circular periphery.

8. The support according to claim 7 in which the base has a triangular periphery.

9. The support according to claim 7 in which the base has an hexagonal periphery.

10. The support according to claim 7 in which the shield is a plate with a non-circular periphery.

11. The support according to claim 8 in which the shield is a plate with a triangular periphery.

12. The support according to claim 9 in which the shield is a plate with an hexagonal periphery.

13. The support according to claim 6 in which the upper end of said stem extends above said shield, and an outer side of the stem adjacent the upper end of said stem tapers upwardly to an annular upper end face, the outer end of said central aperture of said front cap inclining upwardly and inwardly and being detachably engagable with the tapered outer side of said stem to center said needle prior to frictionally engaging said sheath.

14. The support according to claim 13 in which said sheath includes a needle receiving portion and an annular flange extending outwardly from the outer end of said sheath, the diameter of said flange being no greater than the diameter of the outer edge of said annular upper end face, said flange engaging upon said annular upper end face when engaged within the upper end of said stem.

* * * * *